(12) United States Patent
Pantoja De Oliveira Castro et al.

(10) Patent No.: US 8,411,817 B2
(45) Date of Patent: Apr. 2, 2013

(54) METHODS TO DETERMINE LIGHT ELEMENTS CONTENT OF STEEL AND ALLOYS

(75) Inventors: Martha Teresa Pantoja De Oliveira Castro, Ondina (BR); Cristina Maria Assis Lopes Tavarez da Mata Hermida Quintella, Lauro de Freitas (BR); Joao Nazareth Lafayette De Mello Mac-Culloch, Pituba (BR)

(73) Assignees: Petroleo Brasileiro S.A., Rio de Janeiro (BR); Universidade Federal da Bahia, Salvador (BR)

( * ) Notice: Subject to any disclaimer, the term of this patent is extended or adjusted under 35 U.S.C. 154(b) by 267 days.

(21) Appl. No.: 12/740,953

(22) PCT Filed: Oct. 24, 2008

(86) PCT No.: PCT/BR2008/000318
§ 371 (c)(1),
(2), (4) Date: Jul. 23, 2010

(87) PCT Pub. No.: WO2009/055886
PCT Pub. Date: May 7, 2009

(65) Prior Publication Data
US 2010/0284512 A1 Nov. 11, 2010

(30) Foreign Application Priority Data
Oct. 31, 2007 (BR) .................................... 0706233

(51) Int. Cl.
*G01N 23/223* (2006.01)

(52) U.S. Cl. .......................................................... 378/45
(58) Field of Classification Search .............. 378/44–49, 378/57
See application file for complete search history.

(56) References Cited

U.S. PATENT DOCUMENTS
3,501,633 A 3/1970 Hesse et al. ..................... 378/73

FOREIGN PATENT DOCUMENTS
| JP | 11-064254 | 3/1999 |
| JP | 2001-281176 | 10/2001 |
| JP | 2007-178445 | 7/2007 |
| SU | 439741 | 8/1974 |

OTHER PUBLICATIONS

International Search Report for PCT/BR2008/000318, mailed Feb. 6, 2009.
Potts et al, "Atomic spectrometry update. X-ray fluorescence spectrometry", Journal of Analytical Atomic Spectrometry, 2003, 18(10), pp. 1297-1316.

*Primary Examiner* — Courtney Thomas
(74) *Attorney, Agent, or Firm* — Nixon & Vanderhye P.C.

(57) ABSTRACT

The present invention refers to the process of determination of light elements, i.e., molar mass lower than 23, within inorganic materials, by means of spectra analysis between 5 keV and 22 keV, obtained from these materials when exposed to X radiation. Particularly, the invention refers to the direct determination of carbon content in steel and alloys. According to the invention process, the inorganic materials are exposed to X radiation and the spectra are organized as a matrix and mathematically processed using chemometric tools properly selected.

7 Claims, 3 Drawing Sheets

METHODS TO DETERMINE LIGHT ELEMENTS CONTENT OF STEEL AND ALLOYS This application is a national stage of International Patent Application No. PCT/BR2008/000318, filed Oct. 24, 2008 which claims priority to Brazilian Patent Application No. PI 0706233-8, filed Oct. 31, 2007 the entire content of each of which is incorporated herein by reference.

INVENTION FIELD

The invention concerns the process to determine light elements, i.e., molar mass lower than 23, in inorganic materials, by analyzing spectra obtained when irradiating these materials with X radiation. The invention concerns the direct determination of carbon content in steel and alloys. The process comprises irradiating the inorganic materials with X-Rays, organizing the spectra obtained as a data matrix, and using mathematical models with properly selected chemometric tools.

INVENTION BASIS

The determination and quantification of light elements in field conditions by non-destructive testing has been a technological challenge to humanity. Specially, the determination of carbon content in steel and in alloys has been both quite difficult and unavoidable for several processes.

There are several spectroscopic methods wherein the irradiation type varies (source properties, particles, energy range, irradiation method, among others), the sample exposure system (physical state, preparation methods, position, irradiated area, among others), the detection type (radiation or particle or their combinations, energy range, synchronism type, one or more particles, local or remote, in a specific angle or angle integrated, among others). In this specification all spectroscopic techniques that comprise irradiation energy within the X-Ray range, independently of the irradiation type, sample exposition or detection type, shall be denominated by the general name "X-Ray Spectroscopy".

One of the spectroscopy types is the X-Ray Fluorescence Spectrometry that is based on the photoelectric effect of absorption-emission and comprises photons and electrons, where detection may be absolute or relative by energy loss.

Usually, X-Ray Fluorescence Spectrometry, at low energies, shows lines and/or bands usually denominated characteristic emission lines. At higher energies lines and/or band denominated scattering lines of the source are found. [*X-Ray Fluorescence Spectrometry*, $2^a$ edition, R. Jenkins, Wiley-Interscience, New York, 1999, ISBN 0-471-29942-1].

The quantum yield of the photoelectric process of absorption—emission depends on the transition and on the atomic number and, for the same transition, usually increases with the increase of the atomic number atomic [*X-Ray Fluorescence Spectrometry*, $2^a$ edition, R. Jenkins, Wiley-Interscience, New York, 1999, ISBN 0-471-29942-1]. Thus, the detection efficiency of the elements is higher for the elements with higher mass. These traditional analysis processes allow a good discrimination from atomic number 11, i.e., sodium.

The radiation scattering causes several effects. The Rayleigh effect, —elastic scattering (coherent, without energy change and with directional memory) and the Compton effect—inelastic scattering (incoherent, multi-directional and with energy changes) are usually studied.

These interactions depend also on the materials composition. Inelastic scattering increases with the reduction of the average molar mass of the sample.

Thus, materials with low molecular mass elements present low photo-electric effect and high Compton scattering.

Thus, the determination of light elements using characteristic lines requires processes that increase the quantum yield by increasing the radiation source intensity or by increasing the complexity and efficiency of instruments and detection techniques, as synchrotron radiation, particles radiation coincidence, synchronous detection, among others. Nevertheless, these processes have the disadvantages of usually presenting low precision and low accuracy. [Potts PJ et al., *Journal of Analytical Atomic Spectrometry* 18 (10): 1297-1316, 2003] [Alvarez M et al. *X-Ray Spectrometry* 20 (2): 67-71, 1991]. Additionally, they also have the competitive disadvantage of requiring long irradiation times to reach satisfactory signal-to-noise ratios and of being expensive. Furthermore, the use of some of those irradiation pieces of equipment becomes unviable due to their size and the required area and the impossibility to relocate them.

The quenched steel monitoring by X-Rays diffraction at high temperatures has been used to determine the microstructure during heat treatment [Wiessner M et al. *Particle & Particle Systems Characterization* 22 (6): 407-417, 2006]. Austenite and martensite reticule network parameters were determined to infer the carbon content changes through the differences between the quantities of the two phases and the micro-stress. Nevertheless, the determination was indirect and did not include determining the several elements with atomic number lower than 11. Additionally, it did not concern determining carbon content in steels, which requires the accurate determination of the element with atomic number 6, and not its indirect measure by difference between phases or by micro-stress change.

The chemometric or multivariate analysis comprises mathematical treatments of chemical data and its matrices with adequate algorithms. Some non-restrictive examples are Principal Components Analysis (PCA), Partial Least Squares (PLS), Principal Components Regression (PCR), Parallel Factors Analysis (PARAFAC) and Tucker, techniques based on distance like Hierarchic Cluster Analysis (HCA), techniques based on artificial intelligence like Neural Networks and Genetic Algorithms, logic techniques like Fuzzy Logic, among other methods that have been used for decades for complex data treatment. Non-restrictive examples are treatment of spectra obtained by different spectroscopies and spectrometries as Near Infrared Spectroscopy (NIR) [Arvanitoyannis I S et al., *Critical Reviews in Food Science and Nutrition* 45 (3): 193-203, 2005], dynamic interfacial tension by Laser Induced Fluorescence Depolarization [Quintella, C. M. et al., *Journal of Physical Chemistry B, USA, v.* 107, n. 33, p. 8511-8516, 2004.], Mass Spectrometry [Aeschliman D B et al., *Analytical Chemistry* 76 (11): 3119-3125, 2004], X-Ray Spectrometry [Pereira F M V at al., *Journal of Agricultural and Food Chemistry* 54 (16): 5723-5730, 2006], among others.

Nowadays there are several commercial software packages for matrix processing by Data Multivariate Analysis. The user must build their own data matrices and define, for each specific situation, the kind of data processing to be used. The existence of these software packages, by themselves, does not allow making analysis and forecasting results, although they are a powerful tool in the hands of experts and researchers, in order to achieve their different goals.

RELATED TECHNIQUES

Light elements within organic liquid matrices have been determined using Backscattered X-Ray radiation [Molt K et al., *X-Ray Spectrometry* 28 (1): 59-63, 1999]. Molt et al. determined C, H and O in organic liquids using the co-variant method of principal components and DXRS spectra.

The simultaneous determination of lead and sulphur by X-Ray Dispersive Spectrometry with multivariate methods of calibration and neural networks [Facchin 1 et al., *X-Ray Spectrometry* 28 (3): 173-177, 1999] was previously done. Mathematic covariant methodologies were used to correct spectral interferences and inter-element interferences in the quantitative analysis of X-Ray Fluorescence [Nagata N et al. *Química Nova* 24 (4): 531-539, 2001].

Patent application BR PI0400867—Espectrometria de Espalhamento de Raios-X (EERX) Associada á Quimiometria—presents a new analysis method using scattering of X-Rays sources, with resolution improved by chemometric tools to classify standards for environmental analysis and animal metabolism and the quantitative measurement of the molar mass of natural organic polymers.

Patent application BR PI0500177—Espalhamento de Raios-X e Quimiometria para Classifição de Óleos Vegetais, Animals, Minerals e/ou Sintéticos—describes another application of the method concerning oil identification and classification.

Patent application BR PI0500753—Método de Controle de Qualidade de Medicamentos Alternativos (Genéricos e Similares) por Espalhamento de Raios-X—concerns classification of complex organic matrices for pharmaceutical industries or medicine manufacturers, for several fruit species, food in general, paints, greases, plants and polymers.

Patent application BR PI0502763—Método de Quantifiçãgao de Parâmetros da Indústria Petrolífera por Espalhamento de Raios-X e Quimiometria—describes a method to determine crude oil properties by characteristics like aniline point, which indicates the contents of aromatics and paraffins, asphaltene contents, volatile materials, among others, where the samples are liquids or solid tablets.

Patent application BR PI0502861—Método de Quantificação de Alumínio em Sílica por Espalhamento de Raios-X Aliado a Quimiometria—concerns the association of X-Ray Scattering and Chemometrics to improve the quantification of element 13—aluminum within silica matrices, specially the determination of aluminum within zeolytes.

Nevertheless, none of the patent applications or other publications cited before concern or suggest the application of the method to determine elements with atomic number lower than 11 within solid materials neither in inorganic matrices, which are, from a chemical point of view, quite differentiated form organic matrices. Additionally they do not concern the determination of carbon content within steel.

Nowadays, most equipment and piping used in humankind productive and industrial facilities are made of steel, due to its mechanical strength, heat resistance and durability. Nevertheless, with time and use, the steel of said equipment and piping deteriorates and need to undergo repairs and/or to be revamped. For this, the human technology depends on periodic and reliable inspection concerning the quality and integrity of the operating equipment and piping, several of which operate under extreme conditions like high pressures. These inspections aim not only to ensure their operation but also to prevent accidents and environmental damages like leaks, contaminations, etc.

Thus, there is a strong demand for processes that allow to determine, by non-destructive testing and field testing, with high precision and high accuracy, the real conditions of equipment and piping concerning their micro-structure and constitution [Santos, G. B et al, Degradação Micro-Estrutural de Aços Ferríticos Avaliada por PLF-FI, Anais da 29ª Reunião Anual da Sociedade Brasileira de Química. 2006].

When determining light elements content within steels, the carbon content is quite important. It is essential in order to know safely how to repair, weld, recover and even use such equipment and piping.

One of the problems of present technology concerning industrial facilities that have been operating for several years is an incomplete inventory, which may lead to not knowing the type of steel used in equipment and piping. As a consequence, for safety reasons, assumptions during inspection, concerning equipment classification cause the underutilization or even the replacement before the end of the service life. Thus, it is needed and it is essential to provide a method that is fast, non-destructive, low-cost and reliable, a method that allows the identification of the exact steel type of an equipment or piping, especially those that are still in operation and that do not possess documentation with such information.

Additionally, it is quite relevant that this determination take place in the field without shutdown. Thus it is possible to avoid economic and financial losses as well as production decreases that may cause serious consequences to the economic and social development.

It is known that carbon content determination is also essential to evaluate the carbon equivalent for the processes of welding two kinds of steel, allowing to choose the electrode, type and intensity of the heat treatment, temperature range, among other parameters [*AWS D1.1/D1.1M:2006*—Structural Welding Code Steel; Annex I Guideline on Alternative Methods for Determining Preheat; I16 *Detailed Guide, I6.1 Hardness Method*]. The carbon equivalent (CE) calculation uses the manufacture certificate values and, when this is not possible, the specification is made according to the following formula:

$$CE = \% C + \% Mn/6 + (\% Cr + \% Mo + \% V)/5 + (\% Cu + \% Ni)/15$$

This means that when the steel type is not known, it is difficult to determine the pre-heating temperature or to select the electrode type (consumable) to be used in welding processes. The measurement pieces of equipment available in the market do not carry out, in the field, in a fast and practical way, the determination of the carbon content in steel. It is necessary to wait for days the results of the laboratory tests in order to take the proper and safe actions concerning the equipment and piping.

As a non-exclusive example, there are the portable analyzers made by HCG Technology that allow the determination of the content of elements with atomic number above 11, with the advantage that the measurement may be carried out in equipment under operation. Nevertheless, they have the disadvantage of not determining carbon, which has an atomic number of 6.

For some specific conditions, it is possible to determine the steels hardness, allowing one to infer the carbon content of steels in the field by a non-destructive test in the field [ARMCO http://www.armco.com.br/informacoes_tabelas.php—produção e inspeção de aço]. Nevertheless, due to the imprecision inherent of the process, there is the disadvantage of having low reliability. Its results present the disadvantage of being masked by the heat treatments. They also have the additional disadvantage of being masked by the presence of alloy elements in the steel composition.

It is known that it is possible to determine the carbon content using synchrotron radiation equipment. Nevertheless, such equipment not only is massive, but also quite expensive, and thus its use is not feasible to the industries.

Nowadays, the usual processes used to determine the carbon content with high precision have the disadvantage of requiring equipment shutdown and/or destructive sampling for laboratory analysis in siderurgical chromatographs.

One object of the present invention is to develop a process that uses an analysis method that allows with reliability and precision to determine directly the carbon content in steels and in alloys.

Another object of the invention is to provide a process that allows the analysis to be carried out in a non-destructive mode that does not require operation shutdown and that can be used in the field.

SUMMARY OF THE INVENTION

The present invention refers to a process to determine qualitatively and quantitatively elements of molar mass lower than 23 within organic materials, specially the direct determination of carbon in steel and alloys, by means of association of multivariate data analysis, or chemometric analysis, applied to spectra obtained by X-Ray irradiation of materials, especially when using the spectral regions which are not usually used. It was observed that, from the analysis of these spectral regions, which were not considered before, it was possible to detect light elements, molar mass lower than 23, which have low capacity of absorbing and emitting radiation, but high capacity of scattering radiation.

DETAILED DESCRIPTION OF THE INVENTION

Figure 1:
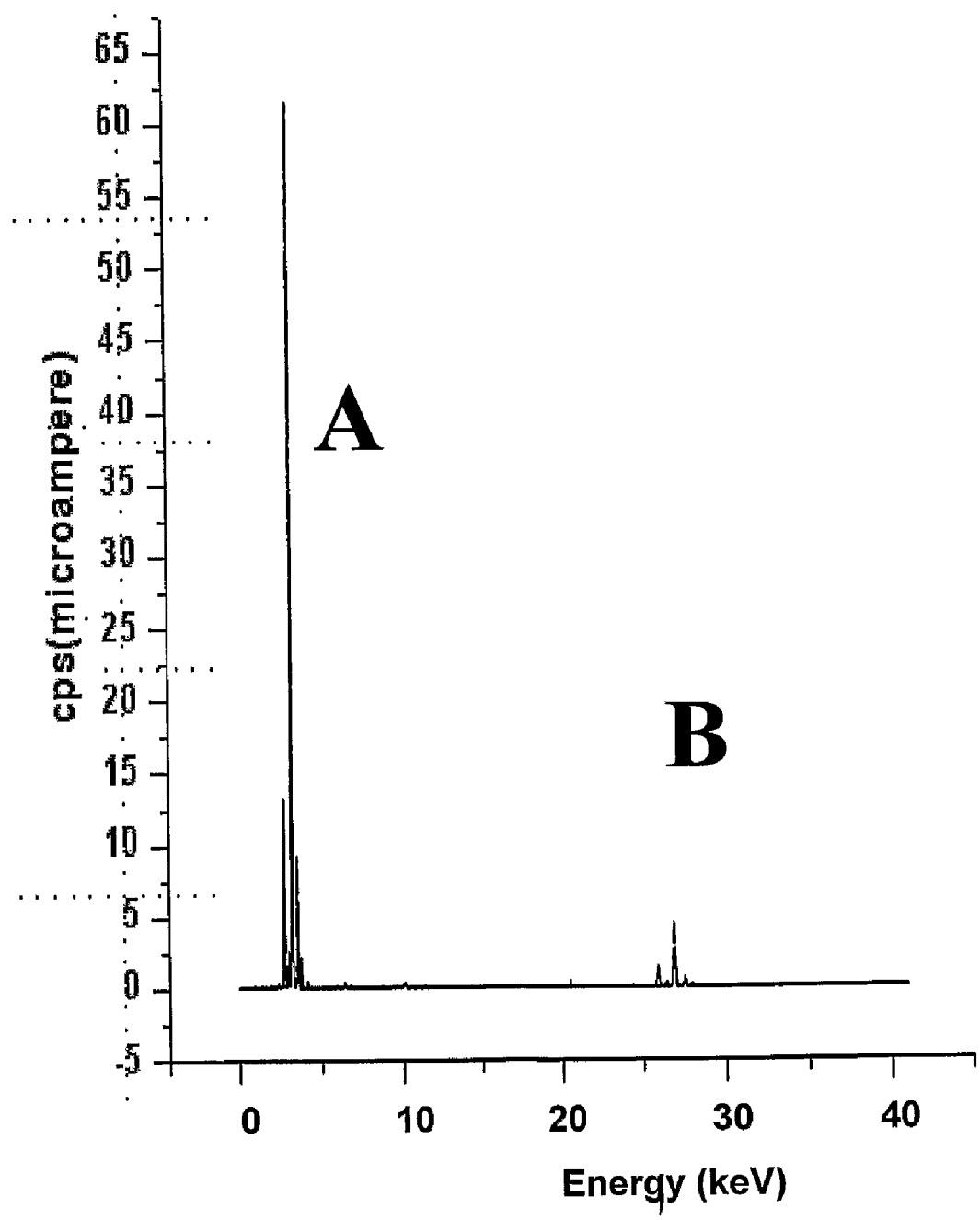
FIG. 1 shows the superposed spectra of X-Rays Fluorescence of six steel samples, with the characteristic emission lines or/and bands and the lines and/or bands of the source scattering, as a non-restrictive Example.

In order to have a better understanding of the invention, a detailed description will be given and referred to the non-restrictive Examples and to the Figures and Table included in this specification, of which they are an integrant part.

According to the process of the present invention, the materials are used directly without previous treatment. The materials are exposed to the radiation source which yields X-Rays, preferable between 5 kV and 50 kV, with an irradiation time between 10 seconds and 100 seconds. The X-Ray spectra are then detected, being either as a function of the energy or as a function of the energy loss. They can be detected in how many replicates as desired, 3 to 5 replicates being more usual.

The spectral regions between 5 keV and 22 keV are analyzed, which includes both the fluorescence and the source scattering. In the past, the scattering region was not considered due to its causing interference in the determination of heavier elements like iron and copper.

Once the desired spectra are obtained, they are organized as a matrix and the data are mathematically processed using chemometric methodology. It is possible to use all the obtained spectra or parts to proceed to the data analysis.

The spectra are mathematically processed by co-variant methodologies. For the exploratory analysis and calibration, what are used are chemometric methods based in projection techniques like Principal Components Analysis (PCA), Partial Least Squares (PLS), Principal Components Regression (PCR), Parallel Factors Analysis (PARAFAC) and Tucker, techniques based on distance like the non-restrictive Example Hierarchic Cluster Analysis (HCA), techniques based on artificial intelligence like Neural Networks and Genetic Algorithms, logic-based techniques like Fuzzy Logic, among other processes.

Both qualitative and quantitative information is obtained. In some conditions, it is possible to use Univariate Treatment of the Correlation. For example, for qualitative analyses are used PCA and HCA, whilst for quantitative analysis are used PLS and PCR.

The result of the data processing is the splitting the materials according to the presence of low molar mass atoms or of their relative concentrations.

Finally, calibration curves are built by mathematical methods like Minimum Squares Regression in the spectral regions that include source scattering and fluorescence, and that enable the process to be modelled.

EXAMPLE 1

Calibration Curve

The following example as the single purpose of illustrating the process here developed, and must not be considered as imitative of the invention.

Samples of six types of different steels were used without any previous treatment. They comprise cylinders with diameter of about 2.5 centimeters and thickness of 1 centimeter. The carbon content was measured in the six standard samples of steel. The carbon content varied from 0.08% to 0.50%.

The samples were obtained randomly in a larger ensemble, having several manufacture dates and with several degrees of exposure to the atmospheric environment.

The specification of the metallic materials analyzed according to the present invention is presented in Table 1.

As described before, in order to obtain the X-Ray Fluorescence spectra, the samples were submitted, without any previous treatment, to the polychromatic radiation of a rhodium X-Ray source. The commercial equipment used was a Shimadzu EDX 700, with irradiation time of 100 seconds, applied voltage of 50 kV and variable current.

To ensure the sample representativeness, one of the samples was irradiated on two different faces. It was found that, by changing the irradiated face, the result is quite similar, thus confirming the material homogeneity, FIG. 1 shows the superposed spectra of X-Ray Fluorescence for each of the six steel samples, with typical lines and/or bands and with the source scattering lines and/or bands. The spectral region used for chemometrics ranges from 5.412 keV (Ka Cr) to 22.0 keV.

The data matrix was built so that each line corresponds to the spectrum of each sample and that each column corresponds to their energy values. The data pre processing consisted in centering the matrix at the mean. The exploratory analysis was done by PCA and the calibration by PLS, using the commercial softwares Mathlab 6.5 and The Unscrambler 9.5.

The data exploratory analysis used the algorithms for Principal Component Analysis (PCA) and Hierarchic Cluster Analysis (HCA). The multivariate data calibration used the algorithm for Partial Least Squares (PLS) and Principal Components Regression (PCR).

The analysis methodology was cross-validated. This validation comprises repeating the analysis as many times as there are samples, withdrawing one sample and processing the other samples; then a second sample is withdraw and the first sample is returned to the ensemble; the procedure is repeated until all the samples have been withdrawn and returned to the ensemble.

Figure 2:
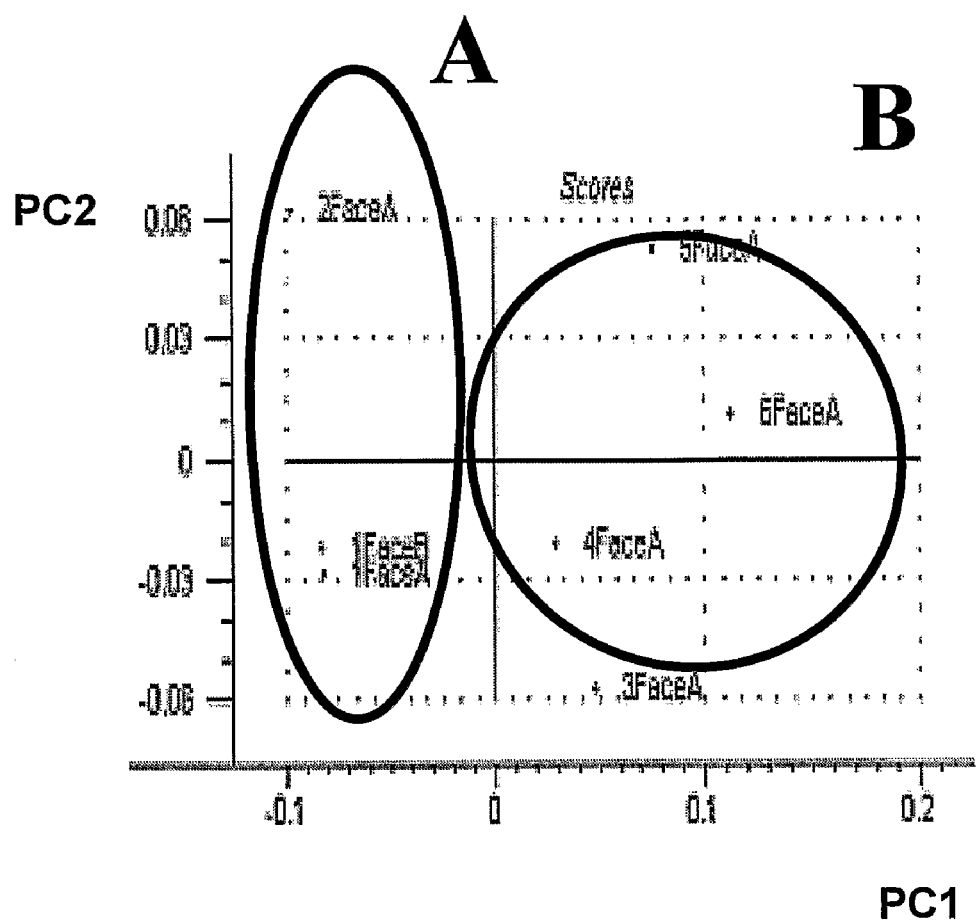
FIG. 2 shows the scores plot after chemometric data treatment of the X-Ray Fluorescence spectra for the six steel samples, as a non-restrictive Example.

FIG. 2 shows the scores plot after chemometric data treatment of the X-Ray Fluorescence spectra for the six steel samples. In this Figure it is observed that the PC1 splits the alloy-steel samples (low PC1 values), grouped and marked with letter A, from the samples of carbon steel (high PC1 values) grouped and marked with letter B. Also in this Figure it is observed that in the vertical axis PC2 the samples are ordered according to their carbon content, i.e., high content for low PC2 values and low content for high PC2 values.

The two principal components of Principal Components Analysis explained 99.85% of the variance and allowed the identification of similar patterns, discriminating the samples with low carbon content from those with high carbon content. The scores plot (FIG. 2) shows the samples ordered according to crescent carbon content in PC2, showing that, for this demonstrative non-restrictive example, it is possible to determine directly and quantitatively the carbon content by the present method, with high precision.

The Partial Least Square Regression applied in the spectral regions including the source scattering and the fluorescence of Fe, Cr and MO, showed that it was possible to build calibrations for carbon content determination with correlation coefficients (r) of the order of 0.98. The method used was cross validation.

Figure 3:
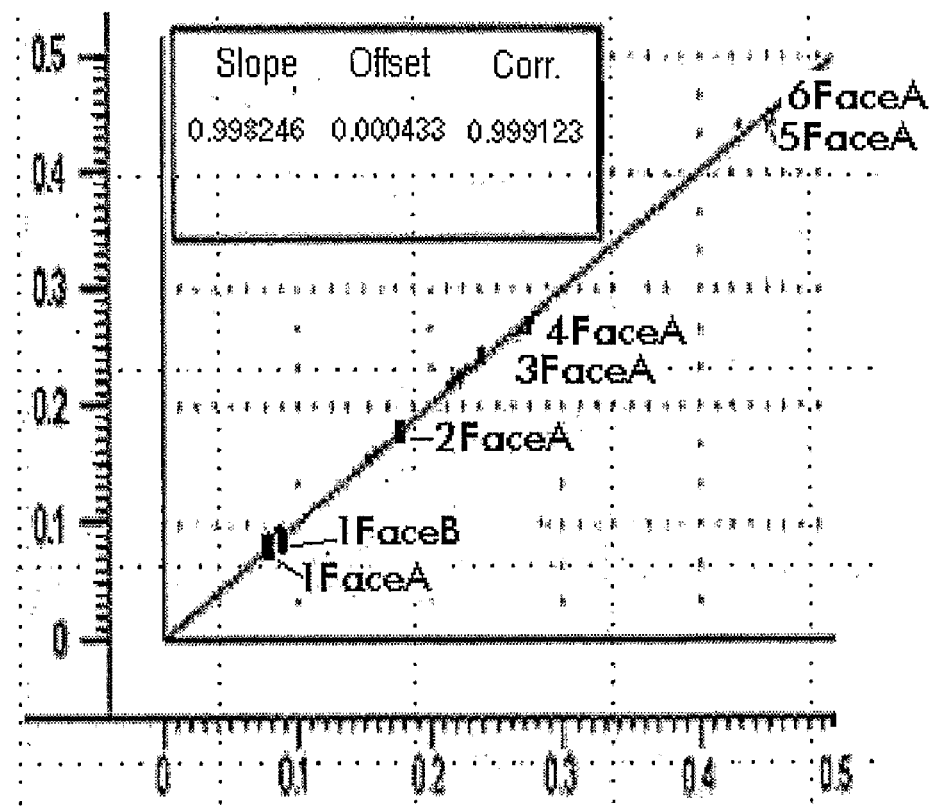
FIG. 3 shows the relation between the measurements obtained by the invention process and the values given by the specification for the carbon content of the steel samples, as a non-restrictive Example.

FIG. 3 shows the relationship between values measured by the present invention process and the values of the steel specifications for the carbon content of the steel samples (Table 1), showing high correlation (r=0.998).

The illustrative example here presented, but not restrictive, used an X-Ray Fluorescence equipment of Shimadzu EDX 700. The standard samples were submitted to the polychromatic radiation of a rhodium X-Ray source, without previous treatment. Identical procedure should be followed to acquire the spectra of the samples. The measurements should be performed in triplicate for each sample and the spectral region analyzed should be between 5.412 keV and 22.0 keV.

b) effect the mathematical processing of the data obtained;
Use the proper software, following the procedure describe in Example 1.
c) use the calibration curve for direct determination of the carbon content, built from the standard samples and properly validated;
In this step the algorithms PLS (Partial Least Squares) or PCR (Principal Components Regression) are used.
d) calculate the reliability levels of the determination using statistical techniques already incorporated in the calibration algorithms: PLS or PCR.

Thus, it becomes obvious that it is possible to obtain reliable information on the material characteristics, using in this technique spectral regions that were not considered in the past. Even more surprising is the possibility of directly determining carbon content in steel alloys with resolution and precision larger than in the processes currently used.

The process of the present invention has the additional advantages of: (a) being a non-destructive process; (b) being applicable in the field; (c) being practical; and (d) having low cost.

Furthermore, it has the competitive advantages that the irradiation time is not required to be long and that it does not require high intensity irradiation sources which are expensive, like synchrotron radiation.

The process of the present invention has also the advantage that the X-Ray spectra obtained are calibrated multivariately, showing high potential for development in order to to be applied to a portable equipment able to be used in the field.

TABLE 1

| N° | Material | Carbon (%) | Manganese (%) | Phosphor (%) | Sulfur (%) | Silicon (%) | Nickel (%) | Chromium (%) | Molybdenum (%) | Copper (%) |
|---|---|---|---|---|---|---|---|---|---|---|
| 1 | Stainless steel S30400 [1] | 0.08 to 0.09 | 2.00 to 2.04 | 0.045 to 0.055 | 0.030 to 0.035 | 1.00 to 1.05 | 8.0 to 11.00 | 18.00 to 20.00 | — | — |
| 2 | Carbon steel 1020 [2] | 0.18 to 0.23 | 0.30 to 0.60 | 0.040 max. | 0.050 max. | — | — | — | — | — |
| 3 | Carbon steel A283 grau C [3] | 0.24 max. | 0.90 max. | 0.035 max. | 0.040 max. | 0.40 max. | — | — | — | 0.20 min. |
| 4 | Carbon steel A36 [4] | 0.28 max. | 0.60 to 0.90 | 0.04 max. | 0.050 max. | 0.40 max. | — | — | — | 0.20 min. |
| 5 | Carbon steel A4140 [2] | 0.38 to 0.43 | 0.75 to 1.00 | 0.035 max. | 0.040 max. | 0.15 to 0.35 | — | 0.80 to 1.10 | 0.15 to 0.25 | — |
| 6 | Carbon steel 1045 [2] | 0.43 to 0.50 | 0.60 to 0.90 | 0.040 max. | 0.050 max. | — | — | — | — | — |

[1] ASTM A 320/A 320M - 07: Standard Specification for Alloy-Steel and Stainless Steel Bolting Materials for Low-Temperature Service
[2] ASTM A 29/A 29M - 05: Standard Specification for Steel Bars, Carbon and Alloy, Hot-Wrought, General Requirements
[3] ASTM A 283/A 283 - 03: Standard Specification for Low and Intermediate Tensile Strength Carbon Steel Plates
[4] ASTM A 36/A 36M - 05: Standard Specification for Carbon Structural Steel.

EXAMPLE 2

Determination of Carbon Content in Samples

When using the process developed by the present invention to determine the carbon content in a steel sample, the procedure to be followed is described as follows:
a) obtain the X-Ray Fluorescence spectra by irradiating the samples;

The invention claimed is:
1. A method for determining light element content of steel and alloys, the method comprising the steps of:
irradiating one or more inorganic materials with an X-Ray in a spectral range corresponding to an energy between 5 keV and 22 keV to obtain a spectra; and
identifying one or more elements with molar mass lower than 23 in the one or more inorganic materials through multivariate data analysis of the spectra obtained by irradiating the one or more inorganic materials.

2. The method according to claim 1, wherein:
a) said one or more elements comprises carbon,
b) said one or more inorganic materials comprises steel or a steel alloy, and
c) said multivariate data analysis comprises chemometric data analysis.

3. The method according to claim 1, wherein the step of irradiating the one or more inorganic materials further comprises the step of non-destructively testing the one or more inorganic materials.

4. The method according to claim 1, wherein the step of identifying one or more elements with molar mass lower than 23 in the one or more inorganic materials through multivariate data analysis of the spectra obtained by irradiating the one or more inorganic materials comprises the steps of:
a) obtaining x-Ray spectra for each sample of the one or more inorganic materials, the spectra resulting from the irradiation of each sample of the one or more inorganic materials;
b) building a data matrix in such a way that each line corresponds to the X-Ray spectrum of each sample and each column corresponds to the energy value of the X-Ray of each sample;
c) mathematically pre-processing the obtained spectra by centering the data matrix at a mean;
d) multivariately calibrating the data matrix to obtain a calibration curve;
e) obtaining further X-Ray spectra by irradiating one or more additional samples of one or more inorganic materials;
f) mathematically processing the further X-Ray spectra;
g) applying the calibration curve to the processed further X-Ray spectra to directly determine a carbon content of the one or more additional samples of one or more inorganic materials;
h) calculating a reliability level of the determination of carbon content of the one or more additional samples of one or more inorganic materials using a statistical technique contained within an algorithm used to multivariately calibrate the data matrix in step d).

5. The method according to claim 1, wherein the multivariate data analysis comprises Principal Component Analysis (PCA) or Hierarchic Cluster Analysis (HCA).

6. The method according to claim 1, wherein the multivariate data analysis comprises Partial Least Squares (PLS) or Principal Components Regression (PCR).

7. The method according to claim 4, wherein the each sample of the one or more inorganic materials have a known carbon content and wherein the one or more additional samples of one or more inorganic materials have an unknown carbon content.

* * * * *